United States Patent
Doi et al.

(10) Patent No.: US 6,391,611 B1
(45) Date of Patent: May 21, 2002

(54) POLYESTER SYNTHASE AND A GENE CODING FOR THE SAME

(75) Inventors: Yoshiharu Doi; Toshiaki Fukui; Hiromi Matsusaki, all of Saitama (JP)

(73) Assignees: Japan Science and Technology Corporation; The Institute of Physical and Chemical Research, both of Saitama (JP)

( * ) Notice: Subject to any disclaimer, the term of this patent is extended or adjusted under 35 U.S.C. 154(b) by 0 days.

(21) Appl. No.: 09/385,742

(22) Filed: Aug. 30, 1999

Related U.S. Application Data

(63) Continuation-in-part of application No. 09/052,339, filed on Mar. 30, 1998, now Pat. No. 5,968,805.

(30) Foreign Application Priority Data

Apr. 1, 1997 (JP) ................................ 9-82965

(51) Int. Cl.[7] .......................... C12N 9/88; C12N 1/20; C12N 15/00; C07H 21/04
(52) U.S. Cl. ................ 435/232; 435/252.3; 435/320.1; 435/325; 536/23.2; 536/23.7
(58) Field of Search .............................. 435/232, 252.3, 435/320.1, 325; 530/350; 536/23.2, 23.7

(56) References Cited

U.S. PATENT DOCUMENTS 5,981,257 A * 11/1999 Fukai et al. ................ 435/232

FOREIGN PATENT DOCUMENTS

WO    WO 97/22711    6/1997

OTHER PUBLICATIONS

Matsusaki et al. [JBC Dec. 1998, 180(24): 6459–6467].*
Matsuzaki et al., Cloning of 2 polyester synthase genes possessed by *Pseudomonas* sp. 61–3,: Nippon Nogeikagaku Kaishi, vol. 71, Mar. 1997, p. 344.
Timm, A. and Steinbuchel, A., "Cloning and molecular analysis of the poly(3–hydroxyalkanoic acid) gene locus of *Pseudomonas aeruginosa* PAOl" European Journal of Biochemistry, vol. 209n No. 1, Oct. 1992, pp. 15–30.
Huisman, G.W. et al., "Metabolism of poly(3–hydroxyalkanoates) (PHAs) by *Pseudomonas oleovorans*" The Journal of Biological Chemistry, vol. 266, No. 4, Feb. 5, 1991, pp. 2191–2198.
Timm, A. et al., "A general method for identification of polyhydroxyalkanoic acid synthase gene from pseudomonads belonging to the rRNA homology group I" Applied Microbiology and Biotechnology, vol. 40, No. 5, Jan. 1994, pp. 669–670.
Steinbuchel, A. et al., "Molecular basis for biosynthesis and accumulation of polyhydroxyalkanoic acids in bacteria" Fems Microbiology Reviews, vol. 103, No. 2–4, Dec. 1992, pp. 219–224.

* cited by examiner

*Primary Examiner*—Ponnathapura Achutamurthy
*Assistant Examiner*—Tekchand Saidha
(74) *Attorney, Agent, or Firm*—Fish & Richardson P.C.

(57) ABSTRACT

The present invention relates to a polypeptide comprising the amino acid sequence of SEQ ID NO:1 or a sequence of SEQ ID NO:1 where in one or more amino acids are deleted, replaced or added, and the polypeptide having polyester synthase activity; a polyester synthase gene comprising DNA coding for the above polypeptide; a recombinant vector comprising the gene; and a transformant transformed with the recombinant vector is also provided.

9 Claims, 1 Drawing Sheet

POLYESTER SYNTHASE AND A GENE CODING FOR THE SAME

CROSS-REFERENCE TO RELATED APPLICATIONS

Figure 1:
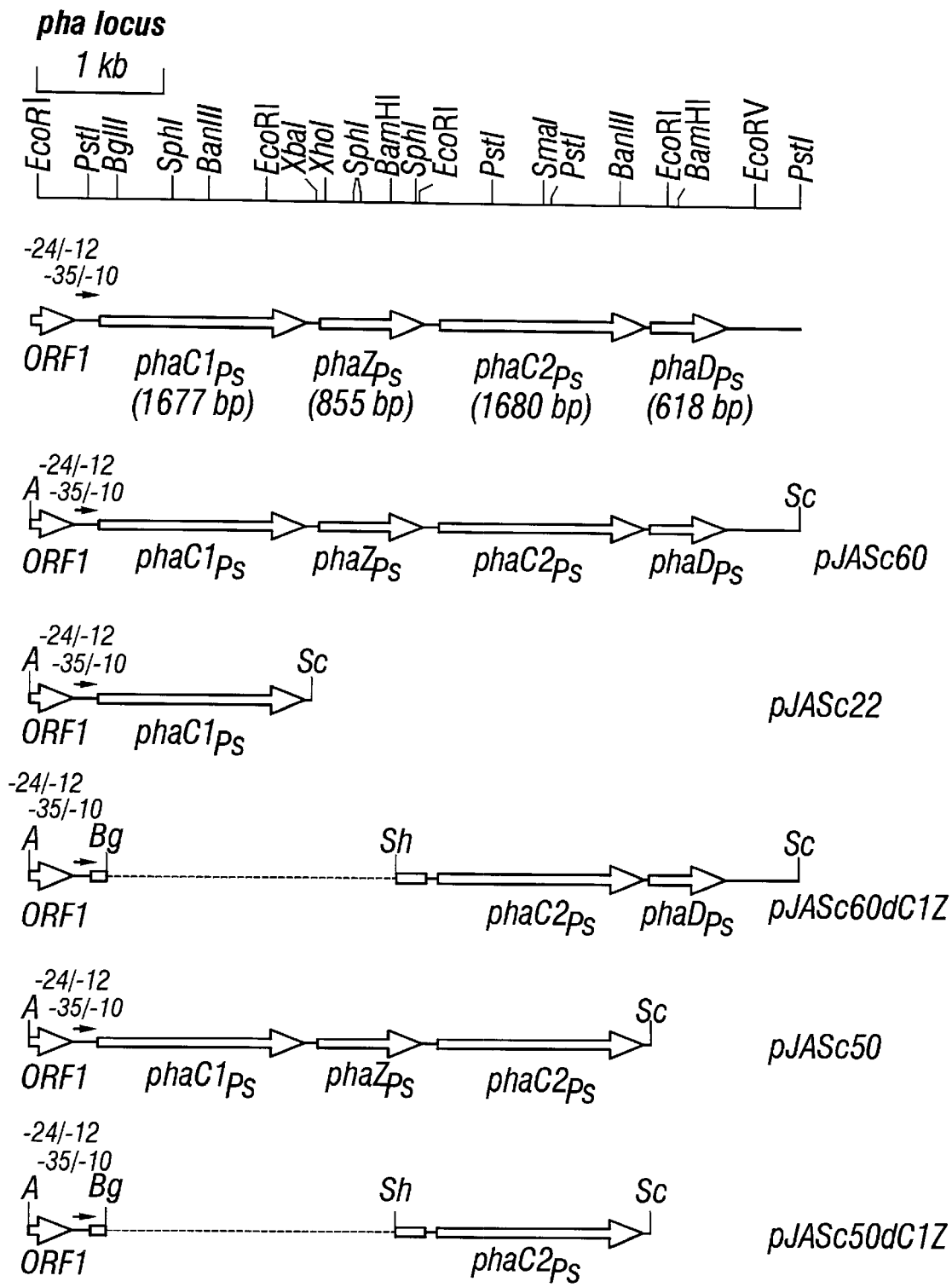

This application is a continuation-in-part, and claims the benefit of priority under 35 USC §120, of U.S. application Ser. No. 09/052,339, filed Mar. 30, 1998, now U.S. Pat. No. 5,968,805 which claims the benefit under 35 U.S.C. §119 of Japanese patent application no. 82965/1977, filed Apr. 1, 1997. The disclosure of the prior applications are considered part of (and are incorporated by reference in) the disclosure of this application.

FIELD OF THE INVENTION

The present invention relates to polyester synthase, a gene coding for the enzyme, a recombinant vector containing the gene, a transformant transformed with the vector, and a process for producing polyester synthase by use of the transformant.

BACKGROUND OF THE INVENTION

Polyesters (e.g., poly-3-hydroxyalkanoic acid) biosynthesized by microorganisms are biodegradable plastics with thermoplasticity ranging widely from rigid matter to viscoelastic rubber.

Poly-3-hydroxybutanoic acid (P(3HB)) is a typical polyester consisting of C4 monomer units, but it is a rigid and brittle polymeric material, so its application is limited. Accordingly, various polyesters such as P(3HB-co-3HV) having (P(3HB)) copolymerized with a C5 monomer unit (3HV) by adding propionic acid etc. to the medium have been prepared and examined to alter the physical properties of the polyester. On the other hand, polyesters consisting of at least C6 monomer units are soft polymeric materials having plasticity.

Polyester-synthesizing microorganisms are roughly divided into 2 groups, that is, those synthesizing polyesters with C3–5 monomer units and those synthesizing polyesters with C6–14 monomer units. The former microorganisms possess a polyester synthase using C3–5 monomer units as the substrate, while the latter microorganisms possess a polyester synthase using C6–14 monomer units as the substrate. Therefore, polyesters with different properties are synthesized by the respective microorganisms.

However, the respective polyesters from such known microorganisms are different in substrate specificity, so with one kind of enzyme given, polyesters (copolymers) having various monomer unit compositions adapted to the object of use are difficult to synthesize.

SUMMARY OF THE INVENTION

The object of the present invention is to provide a polyester synthase with monomer units having a wide range of carbon atoms as the substrate, a gene coding for the enzyme, a recombinant vector containing the gene, a transformant transformed with the vector, and a process for producing the polyester synthase by use of the transformant.

As a result of their eager research, the present inventors succeeded in cloning a polyester synthase gene from a microorganism belonging to the genus Pseudomonas isolated from soil, to arrive at the completion of the present invention.

That is, the present invention is a polypeptide comprising the amino acid sequence of SEQ ID NO:1 or a sequence where in said amino acid sequence, one or more amino acids are deleted, replaced or added, said polypeptide having polyester synthase activity.

Further, the present invention is a polyester synthase gene comprising DNA coding for said polypeptide. The DNA coding for the protein with polyester synthase activity includes, e.g., that of SEQ ID NO:2.

Further, the present invention is a polyester synthase gene comprising the nucleotide sequence of SEQ ID NO:3.

Further, the present invention is a recombinant vector comprising the polyester synthase gene.

Further, the present invention is a transformant transformed with said recombinant vector.

Further, the present invention is a process for producing polyester synthase wherein said transformant is cultured in a medium and polyester synthase is recovered from the resulting culture.

DETAILED DESCRIPTION OF THE INVENTION

Hereinafter, the present invention is described in detail.

(1) Cloning Of The Polyester Synthase Gene

The polyester synthase gene of the present invention is separated from a microorganism belonging to the genus Pseudomonas.

First, genomic DNA is isolated from a strain having the polyester synthase gene. Such a strain includes, e.g., Pseudomonas sp. Any known methods can be used for preparation of genomic DNA. For example, Pseudomonas sp. is cultured in a bouillon medium and then its genomic DNA is prepared by the hexadecyl trimethyl ammonium bromide method (Current Protocols in Molecular Biology, vol. 1, page 2.4.3., John Wiley & Sons Inc., 1994).

The DNA obtained in this manner is partially digested with a suitable restriction enzyme (e.g., Sau3AI, BamHI, BglII etc.). It is then ligated into a vector dephosphorylated by treatment with alkaline phosphatase after cleavage with a restriction enzyme (e.g., BamHI, BglII etc.) to prepare a library.

Phage or plasmid capable of autonomously replicating in host microorganisms is used as the vector. The phage vector includes, e.g., EMBL3, M13, gt11 etc., and the plasmid vector includes, e.g., pBR322, pUC18, and pBluescript II (Stratagene). Vectors capable of autonomously replicating in 2 or more host cells such as *E. coli* and *Bacillus brevis*, as well as various shuttle vectors, can also be used. Such vectors are also cleaved with said restriction enzymes so that their fragment can be obtained.

Conventional DNA ligase is used to ligate the resulting DNA fragment into the vector fragment. The DNA fragment and the vector fragment are annealed and then ligated to produce a recombinant vector.

To introduce the recombinant vector into a host microorganism, any known methods can be used. For example, if the host microorganism is *E. coli*, the calcium chloride method (Lederberg, E. M. et al., J. Bacteriol. 119, 1072 (1974)) and the electroporation method (Current Protocols in Molecular Biology, vol. 1, page 1.8.4 (1994)) can be used. If phage DNA is used, the in vitro packaging method (Current Protocols in Molecular Biology, vol. 1, page 5.7.1 (1994)) etc. can be adopted. In the present invention, an in vitro packaging kit (Gigapack II, produced by Stratagene etc.) may be used.

To obtain a DNA fragment containing the polyester synthase gene derived from Pseudomonas sp., a probe is then prepared. The amino acid sequences of some polyester synthases have already been known (Peoples, O. P. and Sinskey, A. J., J. Biol. Chem., 264, 15293 (1989); Huisman, G. W. et al., J. Biol. Chem., 266, 2191 (1991); Pieper, U. et al., FEMS Microbiol. Lett., 96, 73 (1992); Timm, A. and Steinbuchel, A., Eur. J. Biochem., 209, 15 (1992), etc.). Well-conserved regions are selected from these amino acid sequences, and nucleotide sequences coding for them are estimated to design oligonucleotides. Examples of such oligonucleotides include, but are not limited to, the sequence 5'-CC(G/C)CAGATCAACAAGTT(C/T)TA(C/G)GAC-3' (SEQ ID NO:4) reported by Timm, A. and Steinbuchel, A., Eur. J. Biochem., 209, 15 (1992).

Then, this synthetic oligonucleotide is labeled with a suitable reagent and used for colony hybridization of the above genomic DNA library (Current Protocols in Molecular Biology, vol. 1, page 6.0.3 (1994)).

The E. coli is screened by colony hybridization, and a plasmid is recovered from it using the alkaline method (Current Protocols in Molecular Biology, vol. 1, page 1.6.1 (1994)), whereby a DNA fragment containing the polyester synthase gene is obtained. The nucleotide sequence of this DNA fragment can be determined in, e.g., an automatic nucleotide sequence analyzer such as 373A DNA sequencer (Applied Biosystems) using a known method such as the Sanger method (Molecular Cloning, vol. 2, page 13.3 (1989)).

After the nucleotide sequence was determined by the means described above, the gene of the present invention can be obtained by chemical synthesis or the PCR technique using genomic DNA as a template, or by hybridization using a DNA fragment having said nucleotide sequence as a probe.

(2) Preparation of Transformant

The transformant of the present invention is obtained by introducing the recombinant vector of the present invention into a host compatible with the expression vector used in constructing said recombinant vector.

The host is not particularly limited insofar as it can express the target gene. Examples are bacteria such as microorganisms belonging to the genus Alcaligenes, microorganisms belonging to the genus Bacillus, bacteria such as E. coli, yeasts such as the genera Saccharomyces, Candida etc., and animal cells such as COS cells, CHO cells etc.

If microorganisms belonging to the genus Alcaligenes or bacteria such as E. coli are used as the host, the recombinant DNA of the present invention is preferably constituted such that it contains a promoter, the DNA of the present invention, and a transcription termination sequence so as to be capable of autonomous replication in the host. The expression vector includes pLA2917 (ATCC 37355) containing replication origin RK2 and pJRD215 (ATCC 37533) containing replication origin RSF1010, which are replicated and maintained in a broad range of hosts.

The promoter may be any one if it can be expressed in the host. Examples are promoters derived from E. coli, phage etc., such as trp promoter, lac promoter, PL promoter, PR promoter and T7 promoter. The method of introducing the recombinant DNA into bacteria includes, e.g., a method using calcium ions (Current Protocols in Molecular Biology, vol. 1, page 1.8.1 (1994)) and the electroporation method (Current Protocols in Molecular Biology, vol. 1, page 1.8.4 (1994)).

If yeast is used as the host, expression vectors such as YEp13, YCp50 etc. are used. The promoter includes, e.g., gal 1 promoter, gal 10 promoter etc. To method of introducing the recombinant DNA into yeast includes, e.g., the electroporation method (Methods. Enzymol., 194, 182–187 (1990)), the spheroplast method (Proc. Natl. Acad. Sci. USA, 84, 1929–1933 (1978)), the lithium acetate method (J. Bacteriol., 153, 163–168 (1983)) etc.

If animal cells are used as the host, expression vectors such as pcDNAI, pcDNAI/Amp (produced by Invitrogene) etc. are used. The method of introducing the recombinant DNA into animal cells includes, e.g., the electroporation method, potassium phosphate method etc.

(3) Production of polyester Synthase

Production of the polyester synthase of the present invention is carried out by culturing the transformant of the present invention in a medium, forming and accumulating the polyester synthase of the present invention in the culture (the cultured microorganism or the culture supernatant) and recovering the polyester synthase from the culture.

A conventional method used for culturing the host is also used to culture the transformant of the present invention.

The medium for the transformant prepared from bacteria cush as E. coli etc. as the host includes complete medium or synthetic medium, e.g. LB medium, M9 medium etc. The transformant is aerobically cultured at a temperature ranging from 25 to 37 degrees C. for 12 to 48 hours so that the polyester synthase is accumulated in the microorganism and then recovered.

The carbon source is essential for the growth of the microorganism and includes, e.g., carbohydrates such as glucose, fructose, sucrose, maltose etc.

The nitrogen source includes, e.g., ammonia, ammonium salts such as ammonium chloride, ammonium sulfate, ammonium phosphate etc., peptone, meat extract, yeast extract, corn steep liquor etc. The inorganic matter includes, e.g., monopotassium phosphate, dipotassium phosphate, magnesium phosphate, magnesium sulfate, sodium chloride etc.

Culture is carried out usually under aerobic conditions with shaking at 25 to 37° C. for more than 2 hours after expression is induced. During culture, antibiotics such as ampicillin, kanamycin, ampicillin, tetracycline etc. may be added to the culture.

To culture the microorganism transformed with the expression vector using an inducible promoter, its inducer can also be added to the medium. For example, isopropyl-D-thiogalactopyranoside (IPTG), indoleacrylic acid (IAA) etc. can be added to the medium.

To culture the transformant from animal cells as the host, use is made of a medium such as RPMI-1640 or DMEM which may be supplemented with fetal bovine serum. Culture is carried out usually in 5% CO2 at 30 to 37° C. for 1 to 7 days. During culture, antibiotics such as kanamycin, penicillin etc. may be added to the medium.

Purification of the polyester synthase can be performed by recovering the resulting culture by centrifugation (after disruption in the case of cells) and subjecting it to affinity chromatography, cation or anion exchange chromatography or gel filtration or to a suitable combination thereof.

Whether the resulting purified substance is the desired enzyme is confirmed by conventional methods such as SDS polyacrylamide gel electrophoresis, Western blotting etc.

EXAMPLES

Hereinafter, the present invention is described in more detail with reference to the Examples, which, however are not intended to limit the scope of the present invention.

Example 1

(1) Cloning of the Polyester Synthase Gene From Pseudomonas sp.

First, a genomic DNA library of Pseudomonas sp. was prepared.

Pseudomonas sp. JCM 10015 was cultured overnight in 100 ml bouillon medium (1% meat extract, 1% peptone, 0.5% sodium chloride, pH 7.2) at 30° C. and then genomic DNA was obtained from the microorganism using the hexadecyl trimethyl ammonium bromide method (Current Protocols in Molecular Biology, vol. 1, page 2.4.3 (1994), John Wiley & Sons Inc.).

The resulting genomic DNA was partially digested with restriction enzyme Sau3AI. The vector plasmid used was cosmid vector pLA2917 (ATCC 37355). This plasmid was cleaved with restriction enzyme BglII and dephosphorylated (Molecular Cloning, vol. 1, page 5.7.2 (1989), Cold Spring Harbor Laboratory) and then ligated into the partially digested genomic DNA fragment by use of DNA ligase.

E. coli S 17-1 was transformed with this ligated DNA fragment by the in vitro packaging method (Current Protocols in Molecular Biology, vol. 1, page 5.7.2 (1994)) whereby a genomic DNA library from Pseudomonas sp. was obtained.

To obtain a DNA fragment containing the polyester synthase gene from Pseudomonas sp., a probe was then prepared. An oligonucleotide consisting of the sequence 5'-CC(G/C)CAGATCAACAAGTT(C/T)TA(C/G)GAC-3' (SEQ ID NO:4) reported by Timm, A. and Steinbuchel, A., Eur. J. Biochem., 209, 15 (1992) was synthesized. This oligonucleotide was labeled with digoxigenin using a DIG DNA labeling kit (Boehringer Mannheim) and used as a probe.

Using the probe thus obtained, E. coli carrying a plasmid containing the polyester synthase gene was isolated by colony hybridization from the genomic DNA library from Pseudomonas sp.

When Alcaligenes eutrophus PHB-4 (DSM541) and Pseudomonas putida GPp104 (both of which are strains deficient in an ability to produce polyester) were transformed by the conjugation transfer method with the plasmid containing the polyester synthase gene, both the strains had a reverse ability to produce polyester and showed complementarity.

By recovering the plasmid from the E. coli, a DNA fragment containing the polyester synthase gene was obtained.

The nucleotide sequence of a PstI-XbaI fragment from this fragment was determined by the Sanger method.

As a result, the nucleotide sequence of the 1.8 kbp fragment shown in SEQ ID NO:3 was determined.

By further examining homology to this nucleotide sequence, the polyester synthase gene containing the nucleotide sequence (1680 bp) of SEQ ID NO:2 could be identified in this 1.8 kbp nucleotide sequence. The amino acid sequence encoded by SEQ ID NO:2 is shown in SEQ ID NO:1.

It should be understood that insofar as a protein containing the amino acid sequence of SEQ ID NO:1 or a sequence where in said amino acid sequence, one or more amino acids are deleted, replaced or added has polyester synthase activity, the gene (SEQ ID NO:2 or 3) containing DNA coding for said protein falls under the scope of the polyester synthase gene of the present invention.

Mutations such as deletion, replacement, addition etc. can be induced in the amino acid sequence or nucleotide sequence by the known site-direct mutagenesis method (e.g., Transfomer™ Site-Directed Mutagenesis Kit available from Toyobo).

(2) Preparation of E. coli Transformant

The 1.8 kb PstI-XbaI fragment containing the polyester synthase gene was ligated into the XbaI, PstI site of plasmid vector pBluescript II KS+. The resulting recombinant vector was transformed by the calcium chloride method into Escherichia coli DH5 . The resulting transformant was designated Escherichia coli PX18. By extracting the plasmid from this transformant, the 1.8 kb PstI-Xbal fragment containing the polyester synthase gene can be easily obtained. Escherichia coli PX18 has been deposited as FERM BP-6297 with the National Institute of Bioscience and Human-Technology, Agency of Industrial Science and Technology, Japan.

According to the present invention, there are provided a gene coding for polyester synthase, a recombinant vector containing the gene, and a transformant transformed with the vector. The gene of the present invention codes for a polyester synthase using monomers having a wide range of carbon atoms as the substrate, so it is useful in preparing copolymer polyesters having various physical properties.

Example 2

Introduction

Two types of polyhydroxyalkanoate biosynthesis gene loci (phb andpha) of Pseudomonas sp. 61-3 (JCM 10015), which produces a blend of poly(3-hydroxybutyrate) homopolymer [P(3HB)] and a random copolymer (poly(3-hydroxybutyrate-co-3-hydroxyalkanoates) [P(3HB-co-3HA]) consisting of 3HA units from 4 to 12 carbon numbers, were cloned and analyzed at the molecular level. In the present invention, the substrate specificities of PHA synthases were also evaluated by heterologous expression in PHA-negative mutant of R. eutropha.

Materials and Methods

Bacterial strains, plasmids, and growth conditions. Bacterial strains and plasmids used in this study are listed in Table 1, and the DNA fragments on vectors are illustrated in FIG. 1. Pseudomonas sp. 61-3 and R. eutropha strains were cultivated at 30° C. in a nutrient-rich (NR) medium containing 10 g of meat extract, 10 g of bactopeptone (Difco), and 2 g of yeast extract (Difco) in 1 liter of distilled water. *Escherichia coli* strains were grown at 37° C. on Luria-Bertani (LB) medium (9). When needed, kanamycin (50 mg/liter), tetracycline (12.5 mg/liter), or ampicillin (50 mg/liter) was added to the medium.

DNA manipulations. Isolation of total genomic DNA and plasmids, digestion of DNA with restriction endonucleases, agarose gel electrophoresis, and transformation of *E. coli* were carried out according to standard procedures (11) or the manufacturers. DNA restriction fragments were isolated from agarose gels by using QIAEX II Gel Extraction Kit (QIAGEN). All other DNA-manipulating enzymes were used as recommended by the manufacturers. Genomic DNA libraries of Pseudomonas sp. 61-3 were constructed with Charomid 9-28 (Nippon gene) and pLA2917 (2) by in vitro packaging using Gigapack II (Stratagene). Conjugation of *R. eutropha* with *E. coli* S17-1 harboring broad-host-range plasmids was performed as described by Friedrich et al. (4).

Plasmid construction. Plasmids pJASc22, pJASc60, and pJASc60dC1Z, were constructed as follows: The 2.2-kbp EcoRI-XbaI region containing a gene of the present invention (hereinafter referred to as phaC1$_{Ps}$), and the 6.0-kbp EcoRI-PstI region containing phaC1ZC2D$_{Ps}$ were introduced into pJRD215 as 2.2-kbp and 6.0-kbp ApaI-SacI fragments, to form pJASc22 and pJASc60, respectively (FIG. 1). A plasmid pJASc60dC1Z containing phaC2D$_{Ps}$ was constructed by eliminating a BglII-SphI region from a pBluescript II KS+ derivative plasmid carrying the 6.0-kbp EcoRI-PstI region, and introducing the deleted fragment into pJRD215 at the ApaI and SacI sites (FIG. 1).

Plasmids pJASc50 and pJASc50dC1Z were constructed as follows: The 5.1-kbp EcoRI-BamHI region containing phaC1ZC2$_{Ps}$ was introduced into pJRD215 as a 5.1-kbp ApaI-SacI fragment to form pJASc50 (FIG. 1). A plasmid pJASc50dC1Z containing a gene of the present invention (hereinafter referred to as phaC2$_{Ps}$) was constructed by eliminating a BglII-SphI region from a pBluescript II KS+ derivative plasmid carrying the 5.1-kbp EcoRI-BamHI region, and introducing the deleted fragment into pJRD215 at the ApaI and SacI sites (FIG. 1).

Hybridization experiments. Hybridization was carried out as described by Southern (17). The DNA probes used were a 24-mer synthetic oligonucleotide, 5'-CC(G/C)CAGATCA ACAAG TT(C/T)TA(C/G)GAC-3'(SEQ ID NO 7), whose sequence was based on that of a highly conserved region of the polyester synthases of *R. eutropha* and *P. oleovorans* as described by Timm and Steinbühel (16). Preparation of digoxigenin-labeled probes and the detection of hybridization signals on membranes were carried out with DIG DNA Labeling and Detection Kit (Boehringer Mannheim) and DIG Oligonucleotide Tailing Kit (Boehringer Mannheim).

Nucleotide sequence analysis. DNA fragments to be sequenced were subcloned into pBluescript II KS+. DNA was sequenced by the modified dideoxy chain-termination method basically as described by Sanger et al. (18) with a 310 Genetic Analyzer (Perkin Elmer). The sequencing reaction was performed according to the manual supplied with the dye terminator cycle sequencing kit (Perkin Elmer). The resulting nucleotide sequence was analyzed with SDC-GENETYX genetic information processing software (Software Development Co., Tokyo, Japan).

Production and analysis of pha. Cells were cultivated on a reciprocal shaker (130 strokes/min) at 30° C. for 72 h in 500-ml flasks containing 100 ml of a nitrogen-limited mineral salt (MS) medium, which consisted of 0.9 g of Na$_2$HPO$_4$ 12H$_2$O, 0.15 g of KH$_2$PO$_4$, 0.05 g of NH$_4$Cl, 0.02 g of MgSO$_4$ 7H$_2$O, and 0.1 ml of trace element solution (8). Filter-sterilized carbon sources were added to the medium as indicated in the text. Determination of cellular PHA content and composition by gas chromatography, isolation of the accumulated PHA, fractionation of the isolated polyesters with acetone, and nuclear magnetic resonance (NMR) analysis of polyesters, were carried out in a manner as described by Kato et al. (8, 9).

Results

Cloning and identification of phb and pha loci of Pseudomonas sp. 61-3. To identify the two possible types of polyester synthase genes in Pseudomonas sp. 61-3, genomic DNA fragments from digestion with several restriction enzymes were hybridized with two different gene probes. One probe is a 1.8-kbp fragment carrying phb synthase gene of *R. eutropha* (phbC$_{Re}$), and the other is a 24-mer synthetic oligonucleotide previously used for identification of pha synthase genes from pseudomonads (16). Southern hybridization analysis using each probe showed different patterns of strong signals (14-kbp HindIII-, 20-kbp EcoRI-, 30-kbp BamHI-, 3.5-kbp PstI-, and 6.3-kbp SacI-fragments with the phbC$_{Re}$ probe, and 17-kbp HindIII-, 1.9-kbp EcoRI-, 16-kbp BamHI-, 3.2-kbp PstI-, and 19-kbp SacI-fragments with the 24-mer oligonucleotide probe). This suggested that the two types of polyester synthase genes are located on different DNA loci in Pseudomonas sp. 61-3.

For cloning of the polyester synthase gene hybridized with the phbC$_{Re}$ and the oligonucleotide probes, a genomic sublibrary of 14-kbp HindIII fragments with a cosmid vector Charomid 9-28, and a total genomic DNA library with a cosmid vector pLA2917 (2) from partially digested genomic DNA using Sau3AI were constructed by in vitro packaging. Positive clones isolated by each hybridization screening were further analyzed by Southern hybridization, and a 6.0-kbp HindIII-ApaI and a 6.0-kbp EcoRI-PstI regions were mapped, respectively.

Organization of phb and pha loci. The complete nucleotide sequences of the cloned fragments were determined in both strands. In the 6.0-kbp HindIII-ApaI region (phb locus), four potential open reading frames (ORFs) were identified by computer analysis for protein-coding regions. The nucleotide sequence revealed homologies to genes encoding phb synthase (PhbC$_{Ps}$), β-ketothiolase (PhbA$_{Ps}$), and NADPH-dependent acetoacetyl-CoA reductase (PhbB$_{Ps}$) in *R. eutropha* (Table 2). The phb locus of Pseudomonas sp. 61-3 was constituted of phbBAC$_{Ps}$ operon, which is a different organization from the corresponding operon in *R. eutropha* (phbCAB$_{Re}$).

In the region upstream of phbB$_{Ps}$, another ORF (1,137 bp) was oriented in the opposite direction to the other three genes. The ORF was referred to as phbR$_{Ps}$.

In the 6.0-kbp EcoRI-PstI region (pha locus; SEQ ID NO:8), there are several genes with a similar organization to pha loci of *P. oleovorans* (6) and *P. aeruginosa* (16). Two polyester synthase genes, referred to as phaC1$_{Ps}$ (SEQ ID NO:2) and phaC2$_{Ps}$ (SEQ ID NO:5), are represented as two large open reading frames in this region (FIG. 1). Amino acid sequences encoded by phaC1$_{Ps}$ and phaC2$_{Ps}$ are shown in SEQ ID NOS: 1 and 6, respectively. The two PHA synthases of Pseudomonas sp. 61-3 exhibited 53.2% identity each other, which is similar to the homology between the two synthases of *P. oleovorans* (6). Putative PHA depolymerase is encoded by phaZ$_{Ps}$ located between phaC1$_{Ps}$ and phaC2$_{Ps}$ in Pseudomonas sp. 61-3. An ORF was also identified downstream of phaC2$_{Ps}$ of which deduced amino acid sequence was similar to that of ORF3 of *P. aeruginosa* (Table 2) (16), then it was designated as phaD$_{Ps}$. ORF1 upstream of phaC1$_{Ps}$ was similar to the 3'-terminal region of ORF2 of *P. aeruginosa* (81.7% identity for the C-terminal 93 amino acids) (16). Two nucleotide sequences resembling the *E. coli*-35 to -10 consensus sequence of $\sigma^{70}$-dependent promoter and the *E. coli* -24 to -12 consensus sequence of $\sigma^{54}$-dependent promoter were found upstream of phaC1$_{Ps}$, although their relevance has not been yet explored.

Complementation studies and heterologous expression. To confirm whether the cloned fragments have functionally active PHA biosynthesis genes, heterologous expression of the genes was investigated in the PHA-negative mutants, *R. eutropha* PHB 4 (12). Plasmids pJASc60, pJASc22, pJASc60dC1Z, pJASc50 and pJASc50dC1Z harboring the PHA synthase gene were constructed as described Materials and Methods section. These plasmids were mobilized from *E. coli* Si7-1 to *R. eutropha* PHB 4. The transconjugants were cultivated under nitrogen-limiting conditions in MS medium to promote the PHA biosynthesis from gluconate, octanoate, dodecanoate, or tetradecanoate as a sole carbon source, and were analyzed by gas chromatography to determine the content and composition of the accumulated PHA.

Table 3 shows the results of PHA accumulation in the recombinant strains of *R. eutropha* PHB 4. The plasmids, pJASc22, pJASc60, pJASc60dC1Z, pJASc50 and pJASc50dC1Z could complement the deficiency of polyester synthases in both the mutant strains, and conferred the ability to accumulate PHA on the hosts.

The recombinant strains of PHB 4 harboring pJASc60, pJASc22, pJASc60dC1Z, pJASc50 and pJASc50dC1Z produced P(3HB) homopolymer from gluconate, while the strains produced P(3HB-co-3HA) copolymer consisting of 3HA of $C_4$- to $C_{12}$-monomer units from octanoate, dodecanoate, or tetradecanoate with relatively high 3HB contents (Table 3). 3HB compositions of 30 to 70 mol % were incorporated into the copolymers synthesized by the strains harboring pJASc22, pJASc60dC1Z, pJASc50 and pJASc50dC1Z from the alkanoates (Table 3). Interestingly, PHB 4/pJASc60 produced copolymers composed of much higher 3HB fraction (about 90 mol % 3HB) from octanoate and tetradecanoate. In order to determine whether the polyesters synthesized by PHB 4 strains carrying PHA synthase genes from alkanoates are random copolymers or not, the parameter D values were calculated based on the sequence distribution of 3HB and 3HA units by $^{13}$C-NMR analysis as described by Kamiya et al. (7), which suggested that these polyesters are random copolymers of 3HB and 3HA units (1.4 to 1.6 of D values). As a consequence, both PhaC1$_{Ps}$ and PhaC2$_{Ps}$ of Pseudomonas sp. 61-3 were found to be able to incorporate a wide compositional range of 3HA units from $C_4$ to $C_{12}$ into the polyester.

Discussion

*R. eutropha* PHB 4 strain harboring phaC1$_{Ps}$ and/or phaC2$_{Ps}$ produced P(3HB-co-3HA) copolymers consisting of 3HA units of 4 to 12 carbon numbers from alkanoates. These results indicate that both PHA synthases of Pseudomonas sp. 61-3 are able to incorporate 3HB unit into the polyester as well as medium-chain-length 3HA units.

The results described here demonstrate that the polyester synthase gene of the present invention makes it be possible to synthesize P(3HB-co-3HA) random copolymer with a novel composition having a wide range of rigidity or placticity.

FIGURE LEGENDS

FIG. 1. Organization of pha loci in Pseudomonas sp. 61-3 and DNA fragments including pha locus on broad-host-range vector used in this study.

REFERENCES

1. Abe, H. et al., 1994. Int. J. Biol. Macromol. 16: 115–119
2. Allen, L. N., and R. S. Hanson. 1985. J. Bacteriol. 161: 955–962.
3. Davison, J., M. et al., 1987. Gene 51: 275–280.
4. Friedrich, B., C. et al., 1981. J. Bacteriol. 147: 198–205.
5. Hebert, M. D., and J. E. Houghton. 1997. J. Bacteriol. 179: 7834–7842.
6. Huismen, G. W. et al., 1991. J. Biol. Chem. 266: 2191–2198.
7. Kamiya, N., Y. et al., 1989. Macromolecules 22: 1676–1682.
8. Kato, M. et al., 1996. Appl. Microbiol. Biotechnol. 45: 363–370.
9. Kato, M. et al., 1996. Bull. Chem. Soc. Jpn. 69: 515–520.
10. Peoples, O. P., and A. J. Sinskey. 1989. J. Biol. Chem. 264: 15298–15303.
11. Sambrook, J. et al., 1989. Molecular cloning: a laboratory manual, 2nd ed. Cold Spring Harbor Laboratory Press, Cold Spring Harbor, N.Y.
12. Schlegel, H. G. et al., 1970. Microbiol. 71: 283–294.
13. Schubert, P. et al., 1988. J. Bacteriol. 170: 5837–5847.
14. Simon, R. et al., 1983. Bio/Technology 1: 784–791.
15. Slater, S. C. et al., 1988. J. Bacteriol. 170: 4431–4436.
16. Timm, A., and A. Steinbühel. 1992. Eur. J. Biochem. 209: 15–30.
17. Southern, E. M., 1975. J. Mol. Biol. 98: 503–517.
18. Sanger, F., S. et al., 1977. Proc. Natl. Acad. Sci. USA 74: 5463–5467.

TABLE 1

BACTERIAL STRAINS AND PLASMIDS USED IN THIS STUDY.

| Strain or Plasmid | Relevant Characteristics | Source Or Reference(s)[a] |
|---|---|---|
| Strains | | |
| Pseudomonas sp. strain 61-3 | Wild type | JCM 10015 1, 8, 9 |
| R. eutropha PHB 4 | PHA-negative mutant of H16 | DSM 541, 12 |
| E. coli DH5α | deoR endA1 gyrA96 hsdR17 ($r_K^-$ $m_K^+$) relA1 supE thi-1 Δ (lacZYA-argFV169) Δ80ΔlacZΔM15F-λ- | Clontech |
| E. coli S17-1 | recA and tra genes of plasmid RP4 integrated into chromosome; auxotrophic for proline and thiamine | 14 |
| Plasmids | | |
| pLA2917 | Cosmid; $Km^r$ $Tc^r$ RK2 replicon; $Mob^+$ | 2 |
| pJRD215 | Cosmid; $Km^r$ $Sm^r$ RSF1010 replicon; $Mob^+$ | 3 |
| pBluescript II KS+ | $Ap^r$ lacPOZ T7 and T3 promoter | Stratagene |
| pJASc22 | pJRD215 derivative; $phaC1_{Ps}$ | This study |
| pJASc60 | pJRD215 derivative; $phaC1_{Ps}$ $phaZ_{Ps}$ $phaC2_{Ps}$ $phaD_{Ps}$ | This study |
| pJASc60dC1Z | pJRD215 derivative; $phaC2_{Ps}$ $phaD_{Ps}$ | This study |
| pJASc50 | pJRD215 derivative; $phaC1_{Ps}$ $phaZ_{Ps}$ $phaC2_{Ps}$ | This study |
| pJASc50dC1Z | pJRD215 derivative; $phaC2_{Ps}$ | This study |

[a]JCM, Japan Collection of Microorganisms; DSM, Deutsche Sammlung von Mikroorganismen und Zellkulturen GmbH.

TABLE 2

HOMOLOGY OF THE PRODUCTS OF THE PHB AND PHA LOCI OF PSEUDOMONAS sp. STRAIN 61-3 TO PROTEINS OF OTHER BACTERIA

| Gene Product Designation | Size of Putative Gene Product | Homology To Other Gene Products | |
|---|---|---|---|
| | | Designation[a] | Amino acid identity (%) |
| $PhbR_{Ps}$ | 42.3 | OruR | 25.7 |
| $PhbB_{Ps}$ | 26.7 | $PhbB_{Re}$ | 66.1 |
| $PhbA_{Ps}$ | 40.6 | $PhbA_{Re}$ | 65.8 |
| $PhbC_{Ps}$ | 64.3 | $PhbC_{Re}$ | 53.0 |
| $PhaC1_{Ps}$ | 62.3 | $PhaC1_{Po}$ | 83.7 |
| $PhaZ_{Ps}$ | 31.7 | $PhaZ_{Po}$ | 89.0 |
| $PhaC2_{Ps}$ | 62.8 | $PhaC2_{Po}$ | 74.8 |
| $PhaD_{Ps}$ | 23.5 | $PhaD_{Pa}$ | 77.2 |

OruR, transcriptional regulator for ornithine metabolism of *P. aeruginosa* (5); $PhbB_{Re}$, $PhbA_{Re}$, and $PhbC_{Re}$, NADPH-dependent acetoacetyl-CoA reductase, β-ketothiolase, and PHB synthase of *R. eutropha*, respectively (10, 13, 15); $PhaC1_{Po}$, $PhaZ_{Po}$, and $PhaC2_{Po}$, PHA synthase 1, PHA depolymerase, and PHA

TABLE 3

ACCUMULATION OF PHA BY RECOMBINANT R. EUTROPHA PHB 4 STRAINS HARBORING PHA BIOSYNTHESIS GENES OF PSEUDOMONAS sp. STRAIN 61-3[a]

| Plasmid (Relevant Markers) | Substrate | Dry cell Weight (g/l) | PHA Content (wt %) | PHA composition (mol %)[b] | | | | | |
|---|---|---|---|---|---|---|---|---|---|
| | | | | 3HB (C4) | 3HHx (C6) | 3HO (C8) | 3HD (C10) | 3HDD (C12) | 3H5DD (C12') |
| pJASc60 | Gluconate | 0.85 | 12 | 100 | 0 | 0 | 0 | 0 | 0 |
| (phaC1, phaZ, phaC2, phaD) | Octanoate | 0.84 | 6 | 92 | 0 | 8 | 0 | 0 | 0 |
| | Dodecanoate | 0.30 | 6 | 100 | 0 | 0 | 0 | 0 | 0 |
| | Tetradecanoate | 0.69 | 4 | 91 | 0 | 3 | 3 | 3 | 0 |
| pJASc22 | Gluconate | 0.74 | 2 | 100 | 0 | 0 | 0 | 0 | 0 |
| (phaC1) | Octanoate | 0.86 | 13 | 31 | 10 | 59 | 0 | 0 | 0 |
| | Dodecanoate | 0.61 | 5 | 31 | 4 | 23 | 23 | 19 | 0 |

TABLE 3-continued

ACCUMULATION OF PHA BY RECOMBINANT *R. EUTROPHA* PHB 4 STRAINS HARBORING PHA BIOSYNTHESIS GENES OF PSEUDOMONAS sp. STRAIN 61-3[a]

| Plasmid (Relevant Markers) | Substrate | Dry cell Weight (g/l) | PHA Content (wt %) | PHA composition (mol %)[b] | | | | | |
|---|---|---|---|---|---|---|---|---|---|
| | | | | 3HB (C4) | 3HHx (C6) | 3HO (C8) | 3HD (C10) | 3HDD (C12) | 3H5DD (C12') |
| | Tetradecanoate | 0.97 | 14 | 46 | 4 | 21 | 18 | 11 | 0 |
| PJASc60dC1Z | Gluconate | 0.92 | 20 | 100 | 0 | 0 | 0 | 0 | 0 |
| (phaC2, phaD) | Octanoate | 0.74 | 4 | 50 | 7 | 43 | 0 | 0 | 0 |
| | Dodecanoate | 0.34 | 1 | 51 | 0 | 9 | 13 | 27 | 0 |
| | Tetradecanoate | 0.67 | 5 | 44 | 1 | 16 | 15 | 24 | 0 |
| pJASc50 | Gluconate | 0.52 | 2 | 100 | 0 | 0 | 0 | 0 | 0 |
| (phaC1, phaZ, phaC2) | Tetradecanoate | 0.78 | 6 | 62 | 2 | 16 | 13 | 7 | 0 |
| pJASc50dC1Z | Gluconate | 0.98 | 11 | 100 | 0 | 0 | 0 | 0 | 0 |
| (phaC2) | Tetradecanoate | 0.75 | 3 | 69 | 0 | 11 | 10 | 10 | 0 |

[a]Cells were cultivated at 30° C. for 72 h in MS medium containing the sodium salt of gluconate (2% wt/vol), octanoate (0.1% wt/vol × 5), dodecanoate, or tetradecanoate (0.5% wt/vol) as a sole carbon source.
[b]3HB, 3-hydroxybutyrate; 3HHx, 3-hydroxyhexanoate; 3HO, 3-hydroxyoctanoate; 3HD, 3-hydroxy-decanoate; 3HDD, 3-hydroxydodecanoate; 3H5DD, 3-hydroxy-cis-5-dodecenoate.

What is claimed is:

1. An isolated polynucleotide encoding a polypeptide comprising the amino acid sequence shown in SEQ ID NO: 6.

2. An isolated polynucleotide selected from the group consisting of:
   a) SEQ ID NO: 5;
   b) SEQ ID NO: 5, wherein T is U; and
   c) nucleic acid sequences comlementary to a) to b).

3. An isolated polynucleotide selected from the group consisting of:
   a) SEQ ID NO: 8;
   b) SEQ ID NO: 8 wherein T is U; and
   c) nucleic acid sequences complementary to a) or b).

4. A vector containing a polynucleotide of claims 1, 2 or 3.

5. The vector of claim 4, wherein the vector is a viral vector.

6. The vector of claim 4, wherein the vector is a plasmid.

7. A host cell containing a vector of claim 4.

8. The host cell of claim 7, cultured under conditions which allow expression of the polynucleotide.

9. A method for producing polyester synthase comprising:
   (a) culturing the host cell of claim 7 under conditions suitable for expression of said polyester synthase; and
   (b) recovering the polyester synthase accumulated in the culture medium, a body of the host cell or both of them.

* * * * *

SEQUENCE LISTING

<160> NUMBER OF SEQ ID NOS: 8

<210> SEQ ID NO 1
<211> LENGTH: 559
<212> TYPE: PRT
<213> ORGANISM: Pseudomonas

<400> SEQUENCE: 1

```
Met Ser Asn Lys Asn Ser Asp Asp Leu Asn Arg Gln Ala Ser Glu Asn
1               5                   10                  15

Thr Leu Gly Leu Asn Pro Val Ile Gly Leu Arg Gly Lys Asp Leu Leu
            20                  25                  30

Thr Ser Ala Arg Met Val Leu Thr Gln Ala Ile Lys Gln Pro Ile His
        35                  40                  45

Ser Val Lys His Val Ala His Phe Gly Ile Glu Leu Lys Asn Val Met
    50                  55                  60

Phe Gly Lys Ser Lys Leu Gln Pro Glu Ser Asp Asp Arg Arg Phe Asn
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Gly Asn Ser Lys
            100                 105                 110

Leu Ser Glu Gln Asp Ile Asn Arg Ala His Phe Val Ile Thr Leu Met
        115                 120                 125

Thr Glu Ala Met Ala Pro Thr Asn Ser Ala Ala Asn Pro Ala Ala Val
    130                 135                 140

Lys Arg Phe Phe Glu Thr Gly Gly Lys Ser Leu Leu Asp Gly Leu Thr
145                 150                 155                 160

His Leu Ala Lys Asp Leu Val Asn Asn Gly Gly Met Pro Ser Gln Val
                165                 170                 175

Asp Met Gly Ala Phe Glu Val Gly Lys Ser Leu Gly Thr Thr Glu Gly
            180                 185                 190

Ala Val Val Phe Arg Asn Asp Val Leu Glu Leu Ile Gln Tyr Arg Pro
        195                 200                 205

Thr Thr Glu Gln Val His Glu Arg Pro Leu Leu Val Val Pro Pro Gln
    210                 215                 220
```

```
Ile Asn Lys Phe Tyr Val Phe Asp Leu Ser Pro Asp Lys Ser Leu Ala
225                 230                 235                 240

Arg Phe Cys Leu Ser Asn Asn Gln Gln Thr Phe Ile Val Ser Trp Arg
                245                 250                 255

Asn Pro Thr Lys Ala Gln Arg Glu Trp Gly Leu Ser Thr Tyr Ile Asp
                260                 265                 270

Ala Leu Lys Glu Ala Val Asp Val Ser Ala Ile Thr Gly Ser Lys
                275                 280                 285

Asp Ile Asn Met Leu Gly Ala Cys Ser Gly Ile Thr Cys Thr Ala
290                 295                 300

Leu Leu Gly His Tyr Ala Ala Leu Gly Glu Lys Lys Val Asn Ala Leu
305                 310                 315                 320

Thr Leu Leu Val Ser Val Leu Asp Thr Thr Leu Asp Ser Gln Val Ala
                325                 330                 335

Leu Phe Val Asp Glu Lys Thr Leu Glu Ala Ala Lys Arg His Ser Tyr
                340                 345                 350

Gln Ala Gly Val Leu Glu Gly Arg Asp Met Ala Lys Val Phe Ala Trp
                355                 360                 365

Met Arg Pro Asn Asp Leu Ile Trp Asn Tyr Trp Val Asn Asn Tyr Leu
370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Met Phe
                405                 410                 415

Lys Asn Asn Pro Leu Val Arg Ala Asn Ala Leu Glu Val Ser Gly Thr
                420                 425                 430

Pro Ile Asp Leu Lys Gln Val Thr Ala Asp Ile Tyr Ser Leu Ala Gly
                435                 440                 445

Thr Asn Asp His Ile Thr Pro Trp Lys Ser Cys Tyr Lys Ser Ala Gln
                450                 455                 460

Leu Phe Gly Gly Lys Val Glu Phe Val Leu Ser Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Asp Met Pro Ala Thr Ala Asn Glu Trp Gln Glu Asn Ser Thr
                500                 505                 510

Lys His Thr Asp Ser Trp Trp Leu His Trp Gln Ala Trp Gln Ala Glu
                515                 520                 525

Arg Ser Gly Lys Leu Lys Ser Pro Thr Ser Leu Gly Asn Lys Ala
                530                 535                 540

Tyr Pro Ser Gly Glu Ala Ala Pro Gly Thr Tyr Val His Glu Arg
545                 550                 555
```

<210> SEQ ID NO 2
<211> LENGTH: 1680
<212> TYPE: DNA
<213> ORGANISM: Pseudomonas

<400> SEQUENCE: 2

```
atgagtaaca agaatagcga tgacttgaat cgtcaagcct cggaaaacac cttggggctt    60
aaccctgtca tcggcctgcg tggaaaagat ctgctgactt ctgcccgaat ggttttaacc   120
caagccatca acaacccat tcacagcgtc aagcacgtcg cgcattttgg catcgagctg   180
aagaacgtga tgtttggcaa atcgaagctg caaccggaaa gcgatgaccg tcgtttcaac   240
```

-continued

```
gaccccgcct ggagtcagaa cccactctac aaacgttatc tacaaaccta cctggcgtgg      300
cgcaaggaac tccacgactg gatcggcaac agcaaactgt ccgaacagga catcaatcgc      360
gctcacttcg tgatcaccct gatgaccgaa gccatggccc cgaccaacag tgcggccaat      420 ccggcgcgg tcaaacgctt cttcgaaacc ggcggtaaaa gcctgctcga cggcctcaca       480
catctggcca aggacctggt aaacaacggc ggcatgccga ccaggtgga catgggcgct       540 ttcgaagtcg gcaagagtct ggggacgact gaaggtgcag tggttttccg caacgacgtc      600
ctcgaattga tccagtaccg gccgaccacc gaacaggtgc atgagcgacc gctgctggtg      660
gtcccaccgc agatcaacaa gttttatgtg tttgacctga gcccggataa aagcctggcg      720
cgcttctgcc tgagcaacaa ccagcaaacc tttatcgtca gctggcgcaa cccgaccaag      780
gcccagcgtg agtggggtct gtcgacttac atcgatgcgc tcaaagaagc cgtcgacgta      840
gtttccgcca tcaccggcag caaagacatc aacatgctcg cgcctgctc cggtggcatt       900 acctgcaccg cgctgctggg tcactacgcc gctctcggcg agaagaaggt caatgccctg      960 accctttttgg tcagcgtgct cgacaccacc ctcgactccc aggttgcact gttcgtcgat     1020
gagaaaaccc tggaagctgc caagcgtcac tcgtatcagg ccggcgtgct ggaaggccgc     1080
gacatggcca agtcttcgc ctggatgcgc cctaacgacc tgatctggaa ctactgggtc       1140
aacaactacc tgctgggtaa cgagccaccg gtcttcgaca ttctttttctg gaacaacgac    1200 accacccggt tgcctgctgc gttccacggc gatctgatcg aaatgttcaa aaataaccca    1260
ctggtgcgcg ccaatgcact cgaagtgagc ggcacgccga tcgacctcaa acaggtcact    1320
gccgacatct actccctggc cggcaccaac gatcacatca cgccctggaa gtcttgctac    1380
aagtcggcgc aactgttcgg tggcaaggtc gaattcgtgc tgtccagcag tgggcatatc     1440
cagagcattc tgaaccccgcc gggcaatccg aaatacgtt acatgaccag caccgacatg    1500
ccagccaccg ccaacgagtg gcaagaaaac tcaaccaagc acaccgactc ctggtggctg    1560
cactggcagg cctggcaggc cgagcgctcg ggcaaactga aaaagtcccc gaccagcctg    1620
ggcaacaagg cctatccgtc aggagaagcc gcgccgggca cgtatgtgca tgaacgttaa    1680
```

<210> SEQ ID NO 3
<211> LENGTH: 1826
<212> TYPE: DNA
<213> ORGANISM: Pseudomonas

<400> SEQUENCE: 3

```
ctgcagtgct ctctgaacta gaaagcaacg ttgtgcaatt aacggtcacc cgagcagtag       60
tacctggcgg ttgctgtgtg actacacagc tggtcccggt actcgtctca ggacaatgga      120
gcgtcgtaga tgagtaacaa gaatagcgat gacttgaatc gtcaagcctc ggaaaacacc     180
ttggggctta accctgtcat cggcctgcgt ggaaaagatc tgctgacttc tgcccgaatg     240
gttttaaccc aagccatcaa acaacccatt cacagcgtca agcacgtcgc gcattttggc      300
atcgagctga gaacgtgat gtttggcaaa tcgaagctgc aaccggaaag cgatgaccgt      360
cgtttcaacg accccgcctg gagtcagaac ccactctaca aacgttatct acaaacctac      420
ctggcgtggc gcaaggaact ccacgactgg atcggcaaca gcaaactgtc cgaacaggac     480
atcaatcgcg ctcacttcgt gatcaccctg atgaccgaag ccatggcccc gaccaacagt    540
gcggccaatc cggcgcggt caaacgcttc ttcgaaaccg gcggtaaaag cctgctcgac      600
ggcctcacac atctggccaa ggacctggta aacaacggcg gcatgccgag ccaggtggac    660
```

-continued

```
atgggcgctt tcgaagtcgg caagagtctg gggacgactg aaggtgcagt ggttttccgc      720
aacgacgtcc tcgaattgat ccagtaccgg ccgaccaccg aacaggtgca tgagcgaccg      780
ctgctggtgg tcccaccgca gatcaacaag ttttatgtgt ttgacctgag cccggataaa      840
agcctggcgc gcttctgcct gagcaacaac cagcaaacct ttatcgtcag ctggcgcaac      900
ccgaccaagg cccagcgtga gtgggtctg tcgacttaca tcgatgcgct caaagaagcc       960
gtcgacgtag tttccgccat caccggcagc aaagacatca acatgctcgg cgcctgctcc     1020
ggtggcatta cctgcaccgc gctgctgggt cactacgccg ctctcggcga agaaggtc       1080 aatgccctga cccttttggt cagcgtgctc gacaccaccc tcgactccca ggttgcactg     1140
ttcgtcgatg agaaaaccct ggaagctgcc aagcgtcact cgtatcaggc cggcgtgctg     1200
gaaggccgcg acatggccaa agtcttcgcc tggatgcgcc taacgacct gatctggaac      1260 tactgggtca caactacct gctgggtaac gagccaccgg tcttcgacat tctttttctgg    1320 aacaacgaca ccacccggtt gcctgctgcg ttccacggcg atctgatcga aatgttcaaa     1380
aataacccac tggtgcgcgc caatgcactc gaagtgagcg gcacgccgat cgacctcaaa     1440
caggtcactg ccgacatcta ctccctggcc ggcaccaacg atcacatcac gccctggaag    1500
tcttgctaca agtcggcgca actgttcggt ggcaaggtcg aattcgtgct gtccagcagt    1560
gggcatatcc agagcattct gaacccgccg ggcaatccga atcacgtta catgaccagc     1620 accgacatgc cagccaccgc caacgagtgg caagaaaact caaccaagca caccgactcc    1680
tggtggctgc actggcaggc ctggcaggcc gagcgctcgg gcaaactgaa aaagtccccg    1740
accagcctgg caacaaggc ctatccgtca ggagaagccg cgccgggcac gtatgtgcat     1800
gaacgttaag ttgtaggcag tctaga                                          1826
```

<210> SEQ ID NO 4
<211> LENGTH: 24
<212> TYPE: DNA
<213> ORGANISM: Artifical Sequence
<220> FEATURE:
<223> OTHER INFORMATION: Synthetic DNA

<400> SEQUENCE: 4

```
ccscagatca acaagttyta sgac                                              24
```

<210> SEQ ID NO 5
<211> LENGTH: 1683
<212> TYPE: DNA
<213> ORGANISM: Pseudomonas
<220> FEATURE:
<221> NAME/KEY: CDS
<222> LOCATION: (1)...(1683)

<400> SEQUENCE: 5

```
atg aga gag aaa cca acg ccg ggc ttg ctg ccc aca ccc gcg acg ttc        48
Met Arg Glu Lys Pro Thr Pro Gly Leu Leu Pro Thr Pro Ala Thr Phe
  1               5                  10                  15 atc aac gct cag agt gcg att acc ggt ctg cgc ggc cgg gat ctg ttc        96
Ile Asn Ala Gln Ser Ala Ile Thr Gly Leu Arg Gly Arg Asp Leu Phe
             20                  25                  30 tcg acc ctg cgc agc gtg gcc gcc cac ggc ctg cgt cac ccg gtg cgc       144
Ser Thr Leu Arg Ser Val Ala Ala His Gly Leu Arg His Pro Val Arg
         35                  40                  45 agc gcc cgt cat gtt ctg gca ctg ggc ggc cag ttg ggc cgc gtg ctg       192
Ser Ala Arg His Val Leu Ala Leu Gly Gly Gln Leu Gly Arg Val Leu
     50                  55                  60
```

-continued

| | | |
|---|---|---|
| ctg ggc gaa acg ctg cac acg ccg aac ccg aaa gac aat cgc ttt gcg<br>Leu Gly Glu Thr Leu His Thr Pro Asn Pro Lys Asp Asn Arg Phe Ala<br>65                  70                  75                  80 | 240 |
| gac ccg acc tgg aga ctg aat ccg ttt tac cgg cgc agc ctg cag gcc<br>Asp Pro Thr Trp Arg Leu Asn Pro Phe Tyr Arg Arg Ser Leu Gln Ala<br>                85                  90                  95 | 288 |
| tat ctg agc tgg cag aaa cag gtc aaa agc tgg atc gat gaa agc ggc<br>Tyr Leu Ser Trp Gln Lys Gln Val Lys Ser Trp Ile Asp Glu Ser Gly<br>        100                 105                 110 | 336 |
| atg agt gac gat gac cgc gcc cgc gcg cat ttc gtc ttc gca ctg ctc<br>Met Ser Asp Asp Asp Arg Ala Arg Ala His Phe Val Phe Ala Leu Leu<br>                115                 120                 125 | 384 |
| aat gac gcc gtg tcc ccc tcc aat acc ctg ctc aac ccg cta gcg atc<br>Asn Asp Ala Val Ser Pro Ser Asn Thr Leu Leu Asn Pro Leu Ala Ile<br>130                 135                 140 | 432 |
| aag gag ctg ttc aac tcc ggt ggc aac agc ctg gtc cgc ggt ctc agc<br>Lys Glu Leu Phe Asn Ser Gly Gly Asn Ser Leu Val Arg Gly Leu Ser<br>145                 150                 155                 160 | 480 |
| cat tta ttc gac gac ctg atg cac aac aac ggg ctg ccc agt cag gtc<br>His Leu Phe Asp Asp Leu Met His Asn Asn Gly Leu Pro Ser Gln Val<br>                165                 170                 175 | 528 |
| acc aaa cac gcc ttc gag att ggc aag acc gtg gca acc acc gcc ggg<br>Thr Lys His Ala Phe Glu Ile Gly Lys Thr Val Ala Thr Thr Ala Gly<br>                180                 185                 190 | 576 |
| tcc gtg gtg ttt cgc aac gag ctg ctc gag ctg atg cag tac aag ccg<br>Ser Val Val Phe Arg Asn Glu Leu Leu Glu Leu Met Gln Tyr Lys Pro<br>        195                 200                 205 | 624 |
| atg agc gaa aaa cag tac gcc aag ccg ttg ctg atc gtc ccg ccg cag<br>Met Ser Glu Lys Gln Tyr Ala Lys Pro Leu Leu Ile Val Pro Pro Gln<br>210                 215                 220 | 672 |
| att aac aag tac tac att ttc gac ctc agc ccg ggt aac agc ttc gtc<br>Ile Asn Lys Tyr Tyr Ile Phe Asp Leu Ser Pro Gly Asn Ser Phe Val<br>225                 230                 235                 240 | 720 |
| cag tac gca ttg aag aat ggt ctg cag gtg ttc gtg gtc agc tgg cgt<br>Gln Tyr Ala Leu Lys Asn Gly Leu Gln Val Phe Val Val Ser Trp Arg<br>                245                 250                 255 | 768 |
| aac ccg gat gtt cgc cac cgc gaa tgg ggc ctg tcc agt tac gtt gag<br>Asn Pro Asp Val Arg His Arg Glu Trp Gly Leu Ser Ser Tyr Val Glu<br>                260                 265                 270 | 816 |
| gca ctg gaa gaa gca ctg aat gtt tgc cgc gct atc acc ggc gcg cgc<br>Ala Leu Glu Glu Ala Leu Asn Val Cys Arg Ala Ile Thr Gly Ala Arg<br>        275                 280                 285 | 864 |
| gac gtc aat ctg atg ggc gcc tgt gct ggc ggc ctg acc atc gcg gct<br>Asp Val Asn Leu Met Gly Ala Cys Ala Gly Gly Leu Thr Ile Ala Ala<br>290                 295                 300 | 912 |
| ctg caa ggt cat ctg caa gcc aag cgg caa ctg cgg cgg gtc tcc agc<br>Leu Gln Gly His Leu Gln Ala Lys Arg Gln Leu Arg Arg Val Ser Ser<br>305                 310                 315                 320 | 960 |
| gcc agc tac ctg gtc agc ctg ctg gat agc cag ata gac agc ccg gcg<br>Ala Ser Tyr Leu Val Ser Leu Leu Asp Ser Gln Ile Asp Ser Pro Ala<br>                325                 330                 335 | 1008 |
| acg ttg ttc gcc gat gag cag acg ctg gaa gcc gcc aag cgc cat tcc<br>Thr Leu Phe Ala Asp Glu Gln Thr Leu Glu Ala Ala Lys Arg His Ser<br>                340                 345                 350 | 1056 |
| tat caa cga ggt gtg ctc gag ggg cgc gac atg gcg aaa atc ttc gcc<br>Tyr Gln Arg Gly Val Leu Glu Gly Arg Asp Met Ala Lys Ile Phe Ala<br>        355                 360                 365 | 1104 |
| tgg atg cgc ccc aat gac ctg atc tgg aac tac tgg gtc aac aac tac<br>Trp Met Arg Pro Asn Asp Leu Ile Trp Asn Tyr Trp Val Asn Asn Tyr<br>                370                 375                 380 | 1152 |

```
ctg ctg ggc aaa gaa ccg ccg gcc ttc gac att ctg tat tgg aac agt    1200
Leu Leu Gly Lys Glu Pro Pro Ala Phe Asp Ile Leu Tyr Trp Asn Ser
385                 390                 395                 400 gac aac acg cgc ctg cca gcg gca ttc cat ggc gac ctg ctg gac ttc    1248
Asp Asn Thr Arg Leu Pro Ala Ala Phe His Gly Asp Leu Leu Asp Phe
                405                 410                 415 ttc aag cac aat ccg ctg act cac ccc ggc ggg ctg gag gtc tgt ggc    1296
Phe Lys His Asn Pro Leu Thr His Pro Gly Gly Leu Glu Val Cys Gly
            420                 425                 430 acg cct atc gat ttg cag aag gtc aac gta gac agc ttc agc gtg gcc    1344
Thr Pro Ile Asp Leu Gln Lys Val Asn Val Asp Ser Phe Ser Val Ala
        435                 440                 445 ggc atc aac gac cac atc act ccg tgg gac gcg gtg tac cgc tcg acc    1392
Gly Ile Asn Asp His Ile Thr Pro Trp Asp Ala Val Tyr Arg Ser Thr
    450                 455                 460 ctg ctg ctg ggt ggc gac cgg cgc ttc gta ctg tcc aac agc ggg cat    1440
Leu Leu Leu Gly Gly Asp Arg Arg Phe Val Leu Ser Asn Ser Gly His
465                 470                 475                 480 atc cag agc atc ctc aac ccg ccg agc aac ccc aag tcc aac tac atc    1488
Ile Gln Ser Ile Leu Asn Pro Pro Ser Asn Pro Lys Ser Asn Tyr Ile
                485                 490                 495 gag aac ccc aag ctc agt ggc gat cca cgc gcc tgg tat tac gac ggc    1536
Glu Asn Pro Lys Leu Ser Gly Asp Pro Arg Ala Trp Tyr Tyr Asp Gly
            500                 505                 510 acc cat gtc gaa ggt agc tgg tgg cca cgt tgg ctg agc tgg att cag    1584
Thr His Val Glu Gly Ser Trp Trp Pro Arg Trp Leu Ser Trp Ile Gln
        515                 520                 525 gag cgc tcc ggt acc caa cgc gaa acc ctg atg gcc ctt ggt aac cag    1632
Glu Arg Ser Gly Thr Gln Arg Glu Thr Leu Met Ala Leu Gly Asn Gln
    530                 535                 540 aac tat cca ccg atg gag gcg gcg cca ggt acc tac gtg cgc gtg cgc    1680
Asn Tyr Pro Pro Met Glu Ala Ala Pro Gly Thr Tyr Val Arg Val Arg
545                 550                 555                 560 tga                                                                1683
 *

<210> SEQ ID NO 6
<211> LENGTH: 560
<212> TYPE: PRT
<213> ORGANISM: Pseudomonas

<400> SEQUENCE: 6

Met Arg Glu Lys Pro Thr Pro Gly Leu Leu Pro Thr Pro Ala Thr Phe
1               5                   10                  15

Ile Asn Ala Gln Ser Ala Ile Thr Gly Leu Arg Gly Arg Asp Leu Phe
            20                  25                  30

Ser Thr Leu Arg Ser Val Ala Ala His Gly Leu Arg His Pro Val Arg
        35                  40                  45

Ser Ala Arg His Val Leu Ala Leu Gly Gly Gln Leu Gly Arg Val Leu
    50                  55                  60

Leu Gly Glu Thr Leu His Thr Pro Asn Pro Lys Asp Asn Arg Phe Ala
65                  70                  75                  80

Asp Pro Thr Trp Arg Leu Asn Pro Phe Tyr Arg Arg Ser Leu Gln Ala
                85                  90                  95

Tyr Leu Ser Trp Gln Lys Gln Val Lys Ser Trp Ile Asp Glu Ser Gly
            100                 105                 110

Met Ser Asp Asp Arg Ala Arg Ala His Phe Val Phe Ala Leu Leu
        115                 120                 125
```

-continued

```
Asn Asp Ala Val Ser Pro Ser Asn Thr Leu Leu Asn Pro Leu Ala Ile
    130                 135                 140
Lys Glu Leu Phe Asn Ser Gly Gly Asn Ser Leu Val Arg Gly Leu Ser
145                 150                 155                 160
His Leu Phe Asp Asp Leu Met His Asn Asn Gly Leu Pro Ser Gln Val
                165                 170                 175
Thr Lys His Ala Phe Glu Ile Gly Lys Thr Val Ala Thr Thr Ala Gly
            180                 185                 190
Ser Val Val Phe Arg Asn Glu Leu Leu Glu Leu Met Gln Tyr Lys Pro
        195                 200                 205
Met Ser Glu Lys Gln Tyr Ala Lys Pro Leu Leu Ile Val Pro Pro Gln
    210                 215                 220
Ile Asn Lys Tyr Tyr Ile Phe Asp Leu Ser Pro Gly Asn Ser Phe Val
225                 230                 235                 240
Gln Tyr Ala Leu Lys Asn Gly Leu Gln Val Phe Val Ser Trp Arg
                245                 250                 255
Asn Pro Asp Val Arg His Arg Glu Trp Gly Leu Ser Ser Tyr Val Glu
                260                 265                 270
Ala Leu Glu Glu Ala Leu Asn Val Cys Arg Ala Ile Thr Gly Ala Arg
            275                 280                 285
Asp Val Asn Leu Met Gly Ala Cys Ala Gly Gly Leu Thr Ile Ala Ala
        290                 295                 300
Leu Gln Gly His Leu Gln Ala Lys Arg Gln Leu Arg Arg Val Ser Ser
305                 310                 315                 320
Ala Ser Tyr Leu Val Ser Leu Leu Asp Ser Gln Ile Asp Ser Pro Ala
                325                 330                 335
Thr Leu Phe Ala Asp Glu Gln Thr Leu Glu Ala Ala Lys Arg His Ser
            340                 345                 350
Tyr Gln Arg Gly Val Leu Glu Gly Arg Asp Met Ala Lys Ile Phe Ala
        355                 360                 365
Trp Met Arg Pro Asn Asp Leu Ile Trp Asn Tyr Trp Val Asn Asn Tyr
    370                 375                 380
Leu Leu Gly Lys Glu Pro Pro Ala Phe Asp Ile Leu Tyr Trp Asn Ser
385                 390                 395                 400
Asp Asn Thr Arg Leu Pro Ala Ala Phe His Gly Asp Leu Leu Asp Phe
                405                 410                 415
Phe Lys His Asn Pro Leu Thr His Pro Gly Gly Leu Glu Val Cys Gly
            420                 425                 430
Thr Pro Ile Asp Leu Gln Lys Val Asn Val Asp Ser Phe Ser Val Ala
        435                 440                 445
Gly Ile Asn Asp His Ile Thr Pro Trp Asp Ala Val Tyr Arg Ser Thr
    450                 455                 460
Leu Leu Leu Gly Gly Asp Arg Arg Phe Val Leu Ser Asn Ser Gly His
465                 470                 475                 480
Ile Gln Ser Ile Leu Asn Pro Pro Ser Asn Pro Lys Ser Asn Tyr Ile
                485                 490                 495
Glu Asn Pro Lys Leu Ser Gly Asp Pro Arg Ala Trp Tyr Tyr Asp Gly
            500                 505                 510
Thr His Val Glu Gly Ser Trp Trp Pro Arg Trp Leu Ser Trp Ile Gln
        515                 520                 525
Glu Arg Ser Gly Thr Gln Arg Glu Thr Leu Met Ala Leu Gly Asn Gln
    530                 535                 540
```

Asn Tyr Pro Pro Met Glu Ala Ala Pro Gly Thr Tyr Val Arg Val Arg
545                 550                 555                 560

<210> SEQ ID NO 7
<211> LENGTH: 24
<212> TYPE: DNA
<213> ORGANISM: Artifical Sequence
<220> FEATURE:
<223> OTHER INFORMATION: Synthetic DNA

<400> SEQUENCE: 7
ccscagatca acaagttyta sgac                                           24

<210> SEQ ID NO 8
<211> LENGTH: 6029
<212> TYPE: DNA
<213> ORGANISM: Pseudomonas

<400> SEQUENCE: 8

| | | |
|---|---|---|
| gaattcttgc gcgtgcactc tccttccgcc gaagtccagg gccacggcaa acctatcctg | 60 | |
| caatttggca agatcggcgt aggcctgaac aaggtagaac cggccggtca gtacgcactg | 120 | |
| aaattgacct tcgacgacgg ccatgacagc ggcctgttca cctgggatta tctgtaccaa | 180 | |
| ctggcacaac gtcaggaagc actttgggca gattatcttg cagaactcaa agcggctgga | 240 | |
| aagtcccgcg acccaagcga atccatcgtc aagctgatgc tctaattcag gcctcttgct | 300 | |
| ctttagaggg cattttctaa tttcatctgt ttgaatgctc cgctgtgcgg caagcgattg | 360 | |
| gcctgcttgc gaaaaaaatt aaactcgggt aaccaatgga gctggcaagt tccctgcagt | 420 | |
| gctctctgaa ctagaaagca acgttgtgca attaacggtc acccgagcag tagtacctgg | 480 | |
| cggttgctgt gtgactacac agctggtccc ggtactcgtc tcaggacaat ggagcgtcgt | 540 | |
| agatgagtaa caagaatagc gatgacttga atcgtcaagc ctcggaaaac accttggggc | 600 | |
| ttaaccctgt catcggcctg cgtggaaaag atctgctgac ttctgcccga atggttttaa | 660 | |
| cccaagccat caaacaaccc attcacacgc tcaagcacgt cgcgcatttt ggcatcgagc | 720 | |
| tgaagaacgt gatgtttggc aaatcgaagc tgcaaccgga aagcgatgac cgtcgtttca | 780 | |
| acgaccccgc ctggagtcag aacccactct acaaacgtta tctacaaacc tacctggcgt | 840 | |
| ggcgcaagga actccacgac tggatcggca acagcaaact gtccgaacag gacatcaatc | 900 | |
| gcgctcactt cgtgatcacc ctgatgaccg aagccatggc cccgaccaac agtgcggcca | 960 | |
| atccggcggc ggtcaaacgc ttcttcgaaa ccggcggtaa aagcctgctc gacggcctca | 1020 | |
| cacatctggc caaggacctg gtaaacaacg gcggcatgcc gagccaggtg gacatgggcg | 1080 | |
| ctttcgaagt cggcaagagt ctgggacga ctgaaggtgc agtggttttc cgcaacgacg | 1140 | |
| tcctcgaatt gatccagtac cggccgacca ccgaacaggt gcatgagcga ccgctgctgg | 1200 | |
| tggtcccacc gcagatcaac aagttttatg tgtttgacct gagcccggat aaaagcctgg | 1260 | |
| cgcgcttctg cctgagcaac aaccagcaaa cctttatcgt cagctggcgc aacccgacca | 1320 | |
| aggcccagcg tgagtggggt ctgtcgactt acatcgatgc gctcaaagaa gccgtcgacg | 1380 | |
| tagtttccgc catcaccggc agcaaagaca tcaacatgct cggcgcctgc tccggtggca | 1440 | |
| ttacctgcac cgcgctgctg ggtcactacg ccgctctcgg cgagaagaag gtcaatgccc | 1500 | |
| tgacccttt ggtcagcgtg ctcgacacca ccctcgactc ccaggttgca ctgttcgtcg | 1560 | |
| atgagaaaac cctggaagct gccaagcgtc actcgtatca ggccggcgtg ctggaaggcc | 1620 | |
| gcgacatggc caaagtcttc gcctggatgc gccctaacga cctgatctgg aactactggg | 1680 | |

```
tcaacaacta cctgctgggt aacgagccac cggtcttcga cattcttttc tggaacaacg   1740
acaccacccg gttgcctgct gcgttccacg gcgatctgat cgaaatgttc aaaaataacc   1800
cactggtgcg cgccaatgca ctcgaagtga gcggcacgcc gatcgacctc aaacaggtca   1860
ctgccgacat ctactccctg gccggcacca acgatcacat cacgccctgg aagtcttgct   1920
acaagtcggc gcaactgttc ggtggcaagg tcgaattcgt gctgtccagc agtgggcata   1980
tccagagcat tctgaacccg ccgggcaatc cgaaatcacg ttacatgacc agcaccgaca   2040
tgccagccac cgccaacgag tgcaagaaa actcaaccaa gcacaccgac tcctggtggc    2100
tgcactggca ggcctggcag gccgagcgct cgggcaaact gaaaaagtcc ccgaccagcc   2160
tgggcaacaa ggcctatccg tcaggagaag ccgcgccggg cacgtatgtg catgaacgtt   2220
aagttgtagg cagtctagaa gtccgcggca ctcggaggtg ccgcgagccc taccccatac   2280
agccgaggcc aggcctcgag taatctggag cacgctcagg acggcgtgtc cggcggttta   2340
acccacaggg cttctgagat gccgcaaccg ttcatattcc gtactgtcga cctggatggc   2400
caaaccatcc gcaccgcagt acgccccggc aagtctcata tgacgccctt gcttattttc   2460
aatggcatcg gcgccaacct ggagctggcg ttcccgttcg tccaggcgct tgacccggac   2520
ctggaggtga ttgccttcga cgttcccggt gttggcggct catcgacgcc cagcatgcct   2580
taccgctttc ccagtctggc caagctgacc gcgcgcatgc tcgactacct ggactacggg   2640
caagtcaacg tcgtgggcgt ttcctggggt ggagcactgg cccagcagtt tgcttacgac   2700
tatccagagc gctgcaaaaa actggtgctt gcggcaaccg cggcaggctc ctttatggtg   2760
ccgggcaagc cgaaagtgct gtggatgatg gcaagcccca ggcgctatat ccagccctcc   2820
catgtgattc gcattgctcc gctgatctat ggcggatcct ccgtcgcga ccccaatctg    2880 gccgcagaac acgccagcaa agtacgttcg gccggcaagc tgggttacta ctggcagctg   2940
ttcgcgggtc tgggctggac cagcattcat tggctgcaca aaattcatca gcccaccctg   3000
gtgctggccg gtgacgacga cccgctgatc ccgctgatca acatgcgcat gctggcctgg   3060
cgaattccca acgcccagct acacataatc gacgatggtc atttgttcct gattacccgc   3120
gccgaagccg ttgcgccgat catcatgaag tttcttcagg aggagcgtca gcgggcagtg   3180
atgcatccgc acccgacgcc gctcggcaga acttagagtc tcgcggatgt tgaaaggacc   3240
ttcgcctgcg caagaacggg ctggaccgac tatggtgtct gtcttgaatt gatgtgcttg   3300
ttgatggctt gacgaaggag tgttgactca tgagagagaa accaacgccg ggcttgctgc   3360
ccacacccgc gacgttcatc aacgctcaga gtgcgattac cggtctgcgc ggccgggatc   3420
tgttctcgac cctgcgcagc gtggccgccc acggcctgcg tcaccggtg cgcagcgccc    3480 gtcatgttct ggcactgggc ggccagttgg gccgcgtgct gctgggcgaa acgctgcaca   3540
cgccgaaccc gaaagacaat cgcttttgcgg acccgacctg gagactgaat ccgttttacc   3600
ggcgcagcct gcaggcctat ctgagctggc agaaacaggt caaaagctgg atcgatgaaa   3660
gcggcatgag tgacgatgac cgcgcccgcg cgcatttcgt cttcgcactg ctcaatgacg   3720
ccgtgtcccc ctccaatacc ctgctcaacc cgctagcgat caaggagctg ttcaactccg   3780
gtggcaacag cctggtccgc ggtctcagcc atttattcga cgacctgatg cacaacaacg   3840
ggctgcccag tcaggtcacc aaacacgcct tcgagattgg caagaccgtg caaccaccg    3900 ccgggtccgt ggtgtttcgc aacgagctgc tcgagctgat gcagtacaag ccgatgagcg   3960
aaaaacagta cgccaagccg ttgctgatcg tcccgccgcg gattaacaag tactacatt    4020 tcgacctcag cccgggtaac agcttcgtcc agtacgcatt gaagaatggt ctgcaggtgt   4080
```

-continued

```
tcgtggtcag ctggcgtaac ccggatgttc gccaccgcga atggggcctg tccagttacg    4140
ttgaggcact ggaagaagca ctgaatgttt gccgcgctat caccggcgcg cgcgacgtca    4200
atctgatggg cgcctgtgct ggcggcctga ccatcgcggc tctgcaaggt catctgcaag    4260
ccaagcggca actgcggcgg gtctccagcg ccagctacct ggtcagcctg ctggatagcc    4320
agatagacag cccggcgacg ttgttcgccg atgagcagac gctggaagcc gccaagcgcc    4380
attcctatca acgaggtgtg ctcgaggggc gcgacatggc gaaaatcttc gcctggatgc    4440
gccccaatga cctgatctgg aactactggg tcaacaacta cctgctgggc aaagaaccgc    4500
cggccttcga cattctgtat tggaacagtg acaacacgcg cctgccagcg gcattccatg    4560
gcgacctgct ggacttcttc aagcacaatc cgctgactca ccccggcggg ctggaggtct    4620
gtggcacgcc tatcgatttg cagaaggtca acgtagacag cttcagcgtg ccggcatca    4680 acgaccacat cactccgtgg gacgcggtgt accgctcgac cctgctgctg ggtggcgacc    4740
ggcgcttcgt actgtccaac agcgggcata tccagagcat cctcaacccg ccgagcaacc    4800
ccaagtccaa ctacatcgag aaccccaagc tcagtggcga tccacgcgcc tggtattacg    4860
acggcaccca tgtcgaaggt agctggtggc acgttggct gagctggatt caggagcgct    4920
ccggtaccca acgcgaaacc ctgatggccc ttggtaacca gaactatcca ccgatggagg    4980
cggcgccagg tacctacgtg cgcgtgcgct gaattctctc tgcaccacgg tcgggctatt    5040
ggccgtggca tgactcaata accaagaaga ctggatgaaa accgcgacc ggatcctcga    5100 atgtgccctg caactgttca accaaagggg cgaaccgaat gtctccacca tggaagttgc    5160
caatgagatg ggcatcagcc ctggcaacct ctattaccac tttcatggca aggaaccgct    5220
gatcctcggc ttgttcgagc gcttccaggc cgaactggtc ccgctgctcg acccgccggc    5280
ggacgtacaa ctgccgctg gagattattg gctgttcctg cacctgatcg tcgagcgcct    5340
ggcgcactac cgcttcctgt ttcaggacct gtccaacctg gccggacgct accgaaaact    5400
ggccaagggc attcgcaacc tgctcaatgc cttgaagcgt accctggcgt cgttgttggc    5460
gcggttgaaa gcgcaaggac agttggtcag cgacacacag gcgctggggc aactggtcga    5520
gcagatcacc atgacgctgc tgttttcact cgactatcaa aggattcttg atcgcgaggg    5580
agaagtgcgg gtggtggtgt accagatcat gatgctggta gcgccgcacc tgctgccacc    5640
ggtgaaattg gcgacggagc aaatggcgtt gcgatatctg gaggagcatg agtgagagag    5700
ctgagtagga caccagatcg tttcctcgct gatgatcgtt cccacgcgcc gcaaaggaat    5760
gcagcccgtg acgctccgcg tcacaaaagc ggacgcagag cgtccagtga ggcattccca    5820
cgcgggagcg tgggaacgat caattttccg tcagaaacaa aaatgcccga catttacagg    5880
ccgggcgttt ttgtgagccc cgaaaaatca ggactgattg gttggcgtcg gtgaagtcgg    5940
cgcaacagtc ggggtaaccg caggggtcgg tgcagcagcg gagttcgctg tgctgaccgg    6000
agctgcgggg ttggccgcag caactgcag                                      6029
```